United States Patent [19]

Commereuc et al.

[11] Patent Number: 5,792,895
[45] Date of Patent: Aug. 11, 1998

[54] PROCESS FOR THE CONVERSION OF ETHYLENE INTO BUT-1-ENE USING ADDITIVES BASED ON POLYMETHYLENE GLYCOLS AND DERIVATIVES THEREOF

[75] Inventors: Dominique Commereuc, Meudon; Yves Chauvin, Le Pecq; Francois Hugues, Vernaison; Yves Glaize, Saint Symphorien D'Ozon, all of France

[73] Assignees: Institut Francais du Petrole, France; Saudi Basic Industries Corporation, Saudi Arabia

[21] Appl. No.: 842,502

[22] Filed: Apr. 24, 1997

[30] Foreign Application Priority Data

Apr. 26, 1996 [FR] France .................. 96 05401

[51] Int. Cl.$^6$ .................................................. C07C 2/26
[52] U.S. Cl. ................ 585/512; 585/510; 585/511; 585/520; 585/521; 585/522; 585/523; 585/524
[58] Field of Search ................ 585/510, 511, 585/512, 524, 520, 521, 522, 523

[56] References Cited

U.S. PATENT DOCUMENTS

| | | | |
|---|---|---|---|
| 3,879,485 | 4/1975 | Belov et al. | 585/510 |
| 4,532,370 | 7/1985 | Lé Quan et al. | 585/512 |
| 4,615,998 | 10/1986 | Lé Quan et al. | 502/126 |

*Primary Examiner*—Elizabeth D. Wood
*Attorney, Agent, or Firm*—Millen, White, Zelano & Branigan, P.C.

[57] ABSTRACT

The invention concerns an improved process for the conversion of ethylene into but-1-ene, wherein the ethylene is brought into contact with a catalyst obtained by the interaction of an alkyl titanate, possibly mixed with an ether, with a compound of aluminium of the formula $AlR_3$ or $AlR_2H$, and in the presence of an additive formed by at least one polyethylene glycol and/or one of its derivatives such as a monoether or a monoester of polyethylene glycol.

21 Claims, No Drawings

PROCESS FOR THE CONVERSION OF ETHYLENE INTO BUT-1-ENE USING ADDITIVES BASED ON POLYMETHYLENE GLYCOLS AND DERIVATIVES THEREOF

SUMMARY OF THE INVENTION

The present invention concerns an improved process for the synthesis of but-1-ene by the dimerization of ethylene, by virtue of the use of additives based on polyethylene glycols and/or some of the derivatives thereof such as monoethers or monoesters of polyethylene glycols.

In the process for the dimerization of ethylene to give but-1-ene as described in U.S. Pat. Nos. 4,615,998 and 4,615,998, by means of a homogeneous catalyst obtained by the interaction of a preformed mixture of an alkyl titanate and an ether with a compound of aluminium of the formula $AlR_3$ or $AlR_3H$, the ether being selected from the group formed by diethylether, diisopropylether, dibutylether, methyl-t-butylether, tetrahydrofuran, 1,4-dioxan, dihydropyran, and ethylene glycol dimethylether, small amounts of solid polymer are formed, which are deposited on and adhere to the surface of the reactor and the heat exchanger tubes and which are very harmful to good operation of the process as they reduce the heat transfer effects and necessitate frequent stoppages of the reactor in order for them to be removed.

It has now been found that, if the dimerization reaction is conducted in the presence of additives formed by polyethylene glycols and/or some of the derivatives thereof such as monoethers of polyethylene glycols or monoesters of polyethylene glycols the adhesion of the polymer to the walls of the reactor and the exchangers is considerably reduced and the amount of solid by-product polymer is reduced.

The use of such additives is also possible in the absence of ether such as defined above, more polymer is formed but its very weak adhesion makes it easy to remove.

The invention thus concerns an improved process for the conversion of ethylene into but-1-ene, wherein, in a reaction enclosure, the ethylene is brought into contact with a solution of a catalyst obtained by the interacation of at least one alkyl titanate with a compound of aluminium of the formula $AlR_3$ and $AlR_2H$, each of the residues R being a hydrocarbyl radical, and in the presence of at least one additive selected from the group formed by polyethylene glycols and derivatives thereof.

The elements of the catalyst solution are described in U.S. Pat. Nos. 4,532,370 and 4,615,998, the teachings of which are included herein.

The alkyl titanates used in the invention correspond to the general formula $Ti(OR')_4$ in which R' is a branched or straight chain alkyl radical comprising preferably from 2 to 8 carbon atoms. The following may be mentioned by way of example: tetraethyl titanate, tetraisopropyl titanate, tetra-n-butyl titanate and 2-tetraethylhexyl titanate.

In a particularly advantageous fashion to increase the activity and the selectivity of the reaction, the catalyst solution results from the interaction of a preformed mixture of at least one alkyl titanate and at least one ether, with at least one aluminium compound as defined above. The ethers which can be used may be monoethers or polyethers. It is possible, for example, to use diethylether, diisopropylether, dibutylether, methyl-t-butylether, tetrahydrofuran, 1,4-dioxan, dihydropyran and ethylene glycol dimethylether.

The preferred ethers are tetrahydrofuran and/or 1,4-dioxan. They are used alone or in the form of a mixture.

The ethers are used in a molar ratio of from 0 to 10, advantageously from 0.1 to 10 or from 0.5 to 10, preferably from 1 to 5, more particularly from 2 to 4 moles of ether per mole of compound of titanium. Without being bound to any theory, it can be thought that the ether complexes itself on to the titanium, thus permitting it to be hexacoordinated. If the ether is used in ratios of higher than 10 moles of ether per mole of titanium, for example 20 and above, or if it is used as a solvent for the reaction, it is observed that the reaction is considerably slowed down and that its selectivity is less good and even, in some cases, the reaction no longer takes place at all.

The compounds of aluminium which are used to prepare the catalyst are represented by the general formula $AlR3$ or $AlR_2H$ in which R is a hydrocarbyl radical, preferably alkyl, comprising from 2 to 6 carbon atoms. The compound $AlR_3$ is preferred. Triethylaluminium, tripropylaluminium, tri-isobutylaluminium and trihexylaluminium may be mentioned by way of example.

The components of the catalyst may be brought into contact in a hydrocarbon and/or in the but-1-ene produced by dimerization and/or in a by-product or the by-products of the reaction such as hexenes, preferably in the presence of ethylene. The molar ratio between the compound of aluminium and that of titanium is about 1:1 to 20:1 and preferably about 2:1 to 5:1. The concentration of titanium in the solution prepared in that way is advantageously between $10^{-4}$ and 0.5 mole per liter and preferably between $2.10^{-3}$ and 0.1 mole per liter.

The temperature at which preparation of the catalyst is effected is usually between $-10°$ and $+80°$ C., preferably between $-10°$ and $+45°$ C. When ethylene is present in the medium the amount thereof preferably corresponds to saturation of the solution at the temperature considered and at the pressure adopted, 1 bar or more. The catalyst solution obtained in that way can be used as it is or it can be diluted by the addition of the products of the reaction.

The polyethylene glycols and their monoethers which are used in accordance with the invention correspond to the general formula $H(O-CH_2-CH_2)_nOR"$ in which R" is a hydrogen atom or a hydrocarbyl radical, preferably alkyl, comprising from 5 to 30 carbon atoms, and n is an integer of from 4 to 30. The formula of the monoesters of polyethyleneglycols is $H(O-CH_2-CH_2)_nO-(C=O)-R"$. The monoethers and monoesters are the preferred derivatives. Mention may be made by way of example of polyethylene glycols of a molecular mass of 200 to 10,000 or more, monolaurylethers of polyethylene glycols, monostearylethers of polyethylene glycols, monolaurates of polyethylene glycols, and monostearates of polyethylene glycols.

The polyethylene glycols and/or their derivatives may be used as they are or in the form of a solution in a hydrocarbon medium selected from the group formed by hydrocarbons and/or the dimerization product but-1-ene and/or by a or the by-products of the reaction such as hexenes.

Whether it is a continuous or discontinuous process the polyethylene glycols and/or their derivatives, pure or in solution, may be introduced before proceeding with the ethylene dimerization reaction, for example they may be used to effect a treatment for passivation of the walls of the reaction enclosure prior to the reaction being started. The walls of the enclosure are metallic (metals, steels, alloys . . . ) and may have been subjected to protective treatments (polishing, vitrification . . . ) or may have been subjected to anodic protection.

Passivation is effected using any of the known procedures. Advantageously the enclosure is charged with a solution of 20 ppm to 5% by weight of additive in a hydrocarbon medium, contact is maintained preferably with agitation for from 10 minutes to 10 hours, preferably from 30 minutes to 3 hours, at a temperature below the boiling temperature of the solvent, from 20° to 100° C. generally and from 30° to 80° C. preferably. The solution is then generally discharged.

The polyethylene glycols and/or their derivatives, pure or in solution, can also be introduced continuously or discontinuously while the reaction is taking place, for example in the form of a mixture with the solution of the titanate, preferably in the form of a flow which is independent of the catalyst flows. It may be advantageous to combine a preliminary treatment for passivation of the reaction enclosure, followed by continuous or discontinuous injection while the reaction is taking place.

The amount of polyethylene glycols and/or derivatives thereof used during the dimerization reaction may represent from 1 part per million by weight (ppm) to 5% by weight, advantageously 1 ppm to 1%, preferably 20 ppm to 5000 ppm, with respect to the but-1-ene produced, whether that amount is introduced during the reaction (continuous process) or into the enclosure prior to the reaction (discontinuous process).

The ethylene dimerization reaction can be performed at a temperature of from 20° to 150° C., preferably from 20° to 70° C. and still more preferably from 40° to 70° C. The pressure is preferably from 0.5 to 8 MPa.

In a mode of performing the catalytic dimerization reaction discontinuously, the procedure involves introducing into the reactor (reaction enclosure ) which is provided with the usual agitation and cooling systems, the additive with the catalyst solution, for example a selected volume of catalytic solution, prepared as described above, and, independently, a selected volume of a solution of polyethylene glycol and/or derivative of polyethylene glycol, after which it is pressurised by means of ethylene and the temperature is adjusted to the desired value. The reactor is fed with ethylene at constant pressure until the total volume of liquid produced almost completely fills the reactor. The catalyst is destroyed after reaction, for example by the injection of water, ammonia or an amine, and the products of the reaction and the solvents if used are drawn off and separated.

In the case of continuous operation it is advantageously possible to begin each procedure by passivation of the walls of the reactor with a selected volume of a solution of polyethylene glycol and/or derivative of polyethylene glycol. After that solution has been drawn off and the reactor advantageously rinsed with a hydrocarbon, the catalytic solution is injected continuously at the same time as a solution of polyethylene glycol and/or derivative of polyethylene glycol and at the same time as the ethylene. The temperature and pressure are kept constant by means of any usual regulating system. The effluent from the reactor is passed into a system of distillation columns which permits separation on the one hand of the but-1-ene from the ethylene, which is returned to the reactor, and on the other hand the hexenes and the octenes which are by-products of the reaction and of which a part can be passsed into the catalyst preparation section. The column bottom containing the catalyst, the heavy by-products and the additive can be incinerated or else the recovered catalyst is recycled.

It was found that the presence of additive according to the invention makes it possible significantly to increase the operating life of a reactor in a continuous mode, the polymer then being largely removed from the reactor when the effluent is drawn off and/or by being drawn off at the bottom of the reactor where it is deposited.

EXAMPLES

The following Examples illustrate the invention without limiting the scope thereof.

Examples 1 to 6

A series of tests was carried out to determine the inhibiting effect of the polyethylene glycols and the derivatives of polyethylene glycols on the formation and adhesion to the walls of the polymer which is a by-product in the dimerization of ethylene to form but-1-ene. The effect of the production of polymer is very substantial in terms of fouling of the walls of the reactor and the tubes of the exchangers because it limits the heat transfer effects which are indispensable for eliminating the reaction heat. This harmful effect is observed even when the amount of ethylene transformed into polymer is very low in relation to the amount of ethylene which is dimerised to give but-1-ene.

The ethylene dimerization reaction is effected using an autoclave of Grignard type of stainless steel, of a volume of 250 ml provided with a double jacket permitting regulation of the temperature by a circulation of water, and a magnetic stirrer rod.

In each example the catalyst is prepared at a temperature of 25° C. by successively introducing the following into the reactor at atmospheric pressure of ethylene: 25 ml of heptane, 9.8 ml of a solution of 0.5 ml of triethylaluminium in 19.5 ml of heptane (that is to say 1.77 mmole), 2 ml of a 10% solution by volume of tetra-n-butyl titanate in heptane (that is to say 0.59 mmole) and an amount of the additive polyethylene glycol or polyethylene glycol derivative which is variable according to the tests. After 2 minutes of interaction the temperature is raised to 70° C. and the ethylene pressure to 2 MPa.

The dimerization reaction is stopped by the injection of 2 ml of water when about 100 gaseous liters (related to normal conditions) of ethylene have been consumed. The reactor is then depressurized, the gas being recorded in the operating procedure account and collected in a gasometer to be analyzed. After the reactor has been opened, the liquid and solid content thereof is collected and washed with 20 ml of a 10% sulphuric aqueous solution in order to redissolve the catalyst residues. The remaining solid polymer is filtered, dried for one night in a drying oven at 110° C. and weighed.

The results of the test are set out in Table 1 which shows for each test: the nature of the additive, the amount of additive used expressed in parts per million by weight (ppm) with respect to the but-1-ene formed, the activity of the catalyst expressed by the number of moles of ethylene consumed per hour, the amount of polymer formed in ppm with respect to the ethylene transformed, and the physical appearance of the polymer.

Example 1 is a comparative Example in the absence of additive, which is not part of the invention. In comparison it is clear that the use of an additive formed by a polyethylene glycol or a polyethylene glycol derivative has a beneficial effect on the amount of poplymer formed on the one hand, but in particular its adhesion to the walls on the other hand, which is much less, thus facilitating the removal thereof.

TABLE 1

| No | Additive | Additive/but-1-ene (ppm) | Activity (mole C₂/h) | Polymer (ppm) | Appearance |
|---|---|---|---|---|---|
| 1 | without | 0 | 6.0 | 2330 | (a) |
| 2 | Polyglycol 300 | 200 | 6.0 | 1670 | (b) |
| 3 | $H(OCH_2CH_2)_{23}OC_{12}H_{25}$ | 720 | 6.0 | 1190 | (b) |
| 4 | $H(OCH_2CH_2)_{20}OC_{18}H_{37}$ | 750 | 5.8 | 1500 | (b) |
| 5 | $H(OCH_2CH_2)_4OC_{12}H_{25}$ | 225 | 3.4 | 1000 | (b) |
| 6 | $H(OCH_2CH_2)_{23}OCOC_{12}H_{25}$ | 500 | 5.0 | 1600 | (b) |

(a) polymer which clings very firmly to the walls
(b) polymer in the form of a thin layer with a very low level of adhesion

Examples 7 and 8

In the same apparatus as for Examples 1 to 6 and using the same operating conditions and the same mode of operation, the procedure involves employing a catalyst which has been prepared, at a temperature of 25° C., by successively introducing the following into the reactor under an atmospheric pressure of ethylene: 25 ml of heptane, 10 ml of a solution of triethylaluminium in heptane representing 0.9 mmole of triethylaluminium, and 2 ml of a solution in heptane of a mixture of tetra-n-butyl titanate (0.29 mmole) with 2 molar equivalents of tetrahydrofuran. Example 7 is a comparative Example in the absence of additive and is not part of the invention. Example 8 involves introducing into the reactor after the catalyst an additive formed by a polyethylene glycol ether as indicated in Table 2. Comparison of these two Examples again shows the favorable effect of the addition of a derivative of polyethylene glycol, both on the amount of polymer and in particular on the adhesion thereof to the walls.

TABLE 2

| No | Additive | Additive/but-1-ene (ppm) | Activity (mole C₂/h) | Polymer (ppm) | Appearance |
|---|---|---|---|---|---|
| 7 | without | 0 | 4.4 | 45 | (a) |
| 8 | $H(OCH_2CH_2)_{23}OC_{12}H_{25}$ | 280 | 3.3 | 6 | (b) |

(a) polymer which clings very firmly to the walls
(b) polymer with a very low level of adhesion

We claim:

1. A process for the conversion of ethylene to but-1-ene, comprising contacting, in a reactor, under effective conditions, ethylene with a solution of a catalyst resulting from the interaction of at least one alkyl titanate with at least one aluminum compound of the formula $AlR_3$ or $AlR_2H$, each of the residues R being a hydrocarbyl radical, the process being conducted in the presence of at least one additive which is polyethylene glycol or a monoether or monoester thereof.

2. A process according to claim 1 wherein the catalyst solution results from the interaction of a preformed mixture of at least one alkyl titanate and at least one ether, with at least one aluminum compound of the formula $AlR_3$ or $AlR_2H$, each of the residues L being a hydrocarbyl radical, and the ether being diethylether, diisopropylether, dibutylether, methyl-t-butylether, tetrahydrofuran, 1,4-dioxane, dihydropyran, or ethylene glycol dimethylether.

3. A process according to claim 2, wherein the molar ratio between the ether and the titanium compound is less than or equal to 10.

4. A process according to claim 1, wherein the concentration of titanium in the catalyst solution is between $10^{-4}$ and 0.5 mole per liter.

5. A process according to claim 1, wherein the molar ratio between the aluminium compound and the titanium compound is between 1:1 and 20:1.

6. A process according to claim 1, wherein the aluminium compound is $AlR_3$.

7. A process according to claim 1, wherein polyethylene glycol is selected from the group consisting of monoethers of polyethylene glycols and monoesters of polyethylene glycols.

8. A process according to claim 1, wherein the additive is a polyethylene glycol alkyl ether.

9. A process according to claim 1 wherein the additive is a monolaurylether of polyethylene glycol or a monostearylether of polyethylene glycol.

10. A process according to claim 1, wherein the additive is used in the form of a solution in a hydrocarbon medium which is a hydrocarbon, a dimerisation product, a dimerisation reaction by-product or a mixture thereof.

11. A process according to claim 1, wherein the additive is used in the pure state.

12. A process according to claim 1, wherein before conversion, the additive is introduced into the reactor to effect a treatment of passivation of the walls of the enclosure.

13. A process according to claim 1, wherein the additive is introduced while the conversion reaction is taking place, the process being continuous.

14. A process according to claim 1, wherein the process is discontinuous, and the additive is introduced into the reactor with the catalyst solution.

15. A process according to claim 1, wherein the additive is introduced independently of the catalyst solution.

16. A process according to claim 1, wherein the amount of polyethylene glycol and/or polyethylene glycol monoether or monoester used during the conversion reaction is from 1 ppm to 5 % by weight with respect to the but-1-ene produced.

17. A process according to claim 1, wherein the amount of polyethylene glycol and/or polyethylene glycol monoether or monoester used during the conversion reaction is from 1 ppm to 1 % by weight with respect to the but-1-ene produced.

18. A process according to claim 1, wherein the amount of polyethylene glycol and/or polyethylene glycol monoether or monoester used during the conversion reaction is from 20 ppm to 500 with respect to the but-1-ene produced.

19. A process according to claim 1 conducted at a temperature of about 20° to 150° C. and under a pressure of about 0.5 to 8 MPa.

20. A process according to claim 1, wherein the additive is of the formula:

$$H(O-CH_2-CH_2)_nOH,$$

$$H(O-CH_2-CH_2)_nOR'',$$

or $$H(O-CH_2-CH_2)_nO-(C=O)-R''$$

wherein R" is hydrocarbyl and n is at least 4.

21. A process according to claim 20, wherein n is an integer from 4 to 30.

* * * * *